United States Patent [19]

Alexander et al.

[11] Patent Number: 4,826,995

[45] Date of Patent: May 2, 1989

[54] BISMALEIMIDE DERIVATIVES OF HIGHER MOLECULAR WEIGHT POLYOXYALKYLENEAMINES

[75] Inventors: David C. Alexander; George P. Speranza, both of Austin, Tex.

[73] Assignee: Texaco Inc., White Plains, N.Y.

[21] Appl. No.: 125,093

[22] Filed: Nov. 25, 1987

[51] Int. Cl.$^4$ ......................................... C07D 207/452
[52] U.S. Cl. ......................................................... 548/521
[58] Field of Search ................................... 548/546, 521

[56] References Cited

U.S. PATENT DOCUMENTS

| | | | |
|---|---|---|---|
| 3,890,272 | 6/1975 | D'Alelio | 548/546 |
| 3,951,902 | 4/1976 | Jones | 548/546 |
| 4,116,937 | 9/1978 | Jones | 548/546 |
| 4,237,262 | 12/1980 | Jones | 548/546 |
| 4,277,582 | 7/1981 | Mueller | 548/546 |
| 4,564,663 | 1/1986 | Martin | 548/546 |
| 4,579,674 | 4/1986 | Schlicht | 548/546 |
| 4,675,414 | 6/1987 | DeFusco | 548/521 |

FOREIGN PATENT DOCUMENTS

| | | | |
|---|---|---|---|
| 191931 | 12/1985 | European Pat. Off. | 548/546 |
| 206383 | 12/1986 | European Pat. Off. | 548/546 |
| 2165974 | 6/1971 | Fed. Rep. of Germany | 548/546 |
| 2127024 | 6/1971 | Fed. Rep. of Germany | 548/546 |
| 58-15515 | 7/1981 | Japan | 548/546 |
| 58-40374 | 9/1981 | Japan | 548/546 |
| 58-136637 | 2/1982 | Japan | 548/546 |
| 57-205413 | 12/1982 | Japan | 548/546 |
| 58-127735 | 7/1983 | Japan | 548/546 |

OTHER PUBLICATIONS

Harris, et al., J. Macromol. Sci. Chem. A21, 1117–1135 (1984).
White, "Synthesis and Properties of High Molecular--Weight Step-Growth Polymers from Bismaleimides", *Ind. Eng. Chem. Prod. Res. Dev.* 25, 395–400 (1986).
White, et al., "Reaction of Diaminoalkanes with Bismaleimides: Synthesis of Some Unusual Polyimides", *Journal of Applied Polymer Science*, vol. 29, 891–899 (1984).
Shaw & Kinloch, "Toughened Bismaleimide Adhesives", *Int. J. Adhesion*, Jul. 1985, pp. 123–127.
English, "Premium Performance from Polyimides", *ME* Jan. 1986, pp. 14–19.
J. Falbe, *New Synthesis with Carbon Monoxide*, Springer-Verlag, New York, N.Y., 1980, pp. 128–129.

*Primary Examiner*—Mary C. Lee
*Assistant Examiner*—Robert C. Whittenbaugh
*Attorney, Agent, or Firm*—Jack H. Park; Kenneth R. Priem; Cynthia L. Kendrick

[57] ABSTRACT

Novel bismaleimide derivatives of higher molecular weight polyoxyalkyleneamines of the formula:

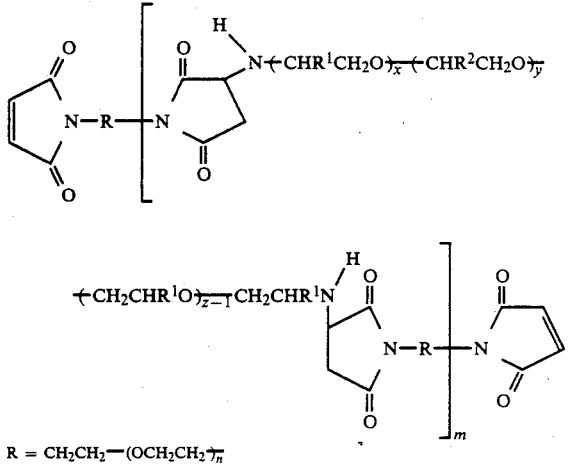

are prepared by reacting higher molecular weight polyoxyalkyleneamines with bismaleimides prepared from low molecular weight oxyethylenediamines. In another embodiment aromatic bismaleimides derivatives are prepared.

7 Claims, No Drawings

BISMALEIMIDE DERIVATIVES OF HIGHER MOLECULAR WEIGHT POLYOXYALKYLENEAMINES

BACKGROUND OF THE INVENTION

1. Technical Field of the Invention

This invention relates to bismaleimides. More particularly, this invention relates to bismaleimide derivatives of higher molecular weight polyoxyalkyleneamines. Still more particularly, this invention relates to bismaleimide derivatives of higher molecular weight polyoxyalkyleneamines prepared by reacting a bismaleimide prepared from a low molecular weight oxyethylenediamine with higher molecular weight (>200) polyoxyalkyleneamines to form bis(maleimidoaspartimide) compounds useful in the preparation of polybismaleimides.

These compounds form clear or transparent orange polymers which can be hard or flexible, have a high temperature of decomposition and can be used for matrix resins in composites.

In a second embodiment of this invention aromatic bismaleimide derivatives are prepared by reaction of polyoxyalkyleneamines with commercially available aromatic bismaleimides. These materials are useful in the preparation of homopolymers and copolymers suitable as matrix resins in composites.

2. Prior Art

The preparation of polybismaleimides by polymerization of bismaleimides is known. Bismaleimide polymers are important primarily for their thermal stability, which usually results from aromaticity in the structure. Although the majority of bismaleimides have therefore been prepared from aromatic diamines, aliphatic compounds can also provide benefits in improved processibility, flexibility and solubility. Bismaleimides have, for example, been prepared from alkylene-diamines (J. Appl. Poly. Sci., 29, 891–899 (1984). Here the polymers were prepared by Michael addition with bisnucleophiles instead of by radical addition of the double bonds to each other.

Bismaleimides have also been prepared from JEFFAMINE ® ED-diamines (U.S. Pat. No. 3,951,902). In U.S. Pat. No. 3,951,902, JEFFAMINE ® ED-900, a polycapped polyoxyethyleneamine, is treated with maleic anhydride to form bismaleamic acid which is cyclodehydrated with acetic anhydride. One disadvantage of this procedure is that it involves removal of dimethylformamide, a high-boiling solvent.

In a series of Japanese patents issued to Mitsui Toatsu Chemicals (JP Nos. 82 205,413; 83 40,374; 83 15,515; 83 136,637), bismaleimides were also prepared from diamines such as 4,7-dioxadecane-1,10-diamine (reduction product of cyanoethylated ethylene glycol) and related diamines; these are used with polybutadiene in preparation of copolymers. The maleimide of triethylene glycol monoamine is also reported in one of these patents.

Use of the oxyethylene group to increase flexibility has been effective in some other types of polymers. In J. Macromol. Sci. Chem., A21, 1117–1135 (1984) there is described preparation of "reactive plasticizers" with acetylene endgroups and internal oxyethylene groups.

Stenzenberger, in German Pat. No. 2,127,024 disclosed the preparation of an aliphatic bismaleimide from 2,2,4-trimethylhexane-1,6-diamine and in German Pat. No. 2,165,974 he described its thermal polymerization.

The use of mixtures of polyoxyalkylene bismaleimides (with molecular weights greater than 400) and aromatic bismaleimides in preparation of flexibilized polybismaleimides is disclosed by de Koning in European Patent Application No. 206,383. While the heat distortion temperature fell with increasing amounts of flexibilizing bismaleimide, the elongation and flexure at break both increased as well.

In U.S. Pat. No. 4,237,262, Jones discloses a low temperature curable composition comprising at least one curable polyimide prepolymer formed by heating an aliphatic oxyalkylene bismaleimide with an aromatic polyamine and at least one aromatic bismaleimide and at least one aliphatic epoxy resin. The reaction product provides at least two functional epoxy groups to provide a low temperature curable composition. In U.S. Pat. No. 3,951,902 Jones et al. disclose a compliant polyimide having superior thermal mechanical properties produced by reacting an aromatic bis(furfurylimide) with an aliphatic ether bis(maleimide) via a Diels-Alder reaction. In U.S. Pat. No. 4,116,937, Jones also discloses a resin system prepared by Michael addition of a mixture of oxyalkylene and aromatic bismaleimides to aromatic diamines. The oxyalkylene bismaleimides have molecular weights of at least 750, and the product is a glassy solid at room temperature. In that case the diamine is always aromatic. It is doubtful that products made from an aromatic-containing compound such as this could be water-soluble.

In European patent application No. 191,931, Nagasaki reveals the use of certain oxyalkylene bismaleimides in rubber compositions.

A curable resin composition is disclosed in Jpn. Kokai Tokkyo Koho JP Nos. 58, 136,637 [83,136,637] 13 August 1983 to Mitsui Toatsu Chemicals. The compound contains an aliphatic imide and polybutadiene containing double bonds.

A Japanese Patent to Mitsui Toatsu Chemicals, Inc. (JP No. 58,127,735 [83,127,735] (Cl. C08G 73/10), July 29, 1983) discloses heat resistant electrical insulators for printed circuit boards are prepared from mixtures of aliphatic polyether bisimides, aromatic bisimides and diamines.

Polymerization of the bismaleimide of dimer diamine, which also contains a hydrocarbon backbone, is disclosed in U.S. Pat. No. 4,564,663. The product polymer is hard and thermally stable.

An article by White in Ind. Eng. Chem. Prod. Res. Dev. 25, 395-400 discusses the fact that bisimides offer potential for the synthesis of high-molecular-weight, step growth polymers. It is stated they are flanked by two electron-withdrawing carbonyl groups and the electrophilic maleimide carbon-carbon-double bond is especially labile to nucleophilic attack and yields Michael type adducts with both amines and thiols. The paper focuses on the requirements for preparation of these polymeric Michael adducts, with additional emphasis on the effects of the enormous structural variety available within the class in the thermal and physical properties of these new resins.

In the art experimental data are available wherein polymers were synthesized which are structurally related to those formed by nucleophilic or Michael addition of diaminoarenes, but which had more flexible backbones and lower glass transition temperature (Tg). See "Reaction of Diaminoalkanes with Bismaleimides: Synthesis of Some Unusual Polyimides", Journal of Applied Polymer Science, Vol. 29, 891–899 (1984).

Shaw and Kinloch have studied the effects of rubber concentration on the morphology, bulk mechanical and thermal properties and the adhesive strength of the bismaleimide by the addition of various amounts of a carboxyl-terminated butadiene (CTBN) rubber toughening agent, and concluded that surprisingly large amounts of CTBN rubber can be added to substantially improve the fracture resistance of the bismaleimide resin without sacrificing other important properties. (See "Toughened Bismaleimide Adhesives", *Int. J. Adhesion,* July 1985, pp. 123–127.)

A growing number of applications for polyimides are discussed in the article titled "Premium Performance from Polyimides" in ME, January 1986, p. 14–19.

In U.S. Pat. No. 4,277,582 Mueller discloses water-insoluble hydrophilic copolymers consisting of a hydrophilic polymer of monoolefinic monomers cross-linked with a major amount of a diolefinic non-hydrophilic macromer.

It appears there is a large market for bismaleimides and a good deal of research in the art has been directed toward studying properties of and better methods for producing these compounds. It is believed the polybismaleimide derivatives of the instant invention, particularly those derived from higher molecular weight polyoxyalkyleneamines reacted with bismaleimides of low molecular weight diamines would exhibit advantages including increased flexibility, reduced brittleness, improved low-temperature properties and would be useful as matrix resins in composites.

Advantages of the first embodiment invention include the fact that aromatic amines, which are in many cases known or suspected to be carcinogenic or otherwise toxic, are not used to prepare the materials.

In the second embodiment of the invention monomers are prepared having a polyoxyalkylene backbone and aromatic bismaleimide termination.

The products resulting from the second embodiment would be of particular interest because they are formed from the reaction of two commercially available materials. The method of preparation disclosed is much easier than the direct route, using maleic anhydride. These materials are useful in the preparation of homopolymers and copolymers that may be suitable as matrix resins in composites.

SUMMARY OF THE INVENTION

In accordance with the present invention, higher molecular weight polyoxyalkyleneamines are reacted with bismaleimides prepared from low molecular weight oxyethylenediamines to afford bis(maleimidoaspartimide) compounds that are useful in the preparation of polybismaleimides.

The reaction is a simple Michael addition that is easy to carry out; it is particularly valuable with propylene oxide capped polyoxyalkyleneamines. Preparation of such materials by conventional methods is difficult because of low product purity resulting from the presence of by-products formed in the cyclodehydration reaction. The low molecular weight bismaleimides react with the propylene oxide-capped diamines in 2/1 ratio to give bis-Michael adducts and these products can be polymerized. The reaction is represented by:

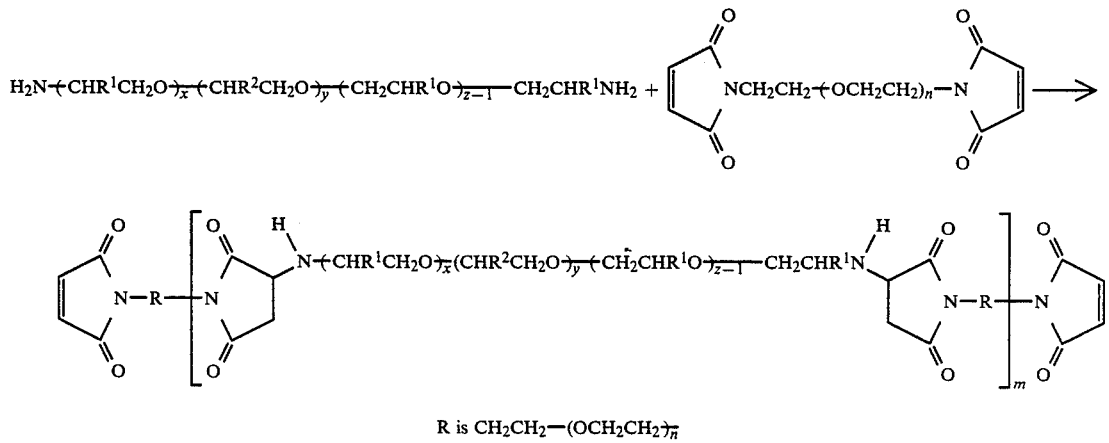

wherein $R^1$ and $R^2$ are independently alkyl or hydrogen, n=1, 2, or 3; and x, y, and z depend on the amine used, and m is predominantly 1.

In another embodiment aromatic bismaleimide derivatives are prepared, having the formula:

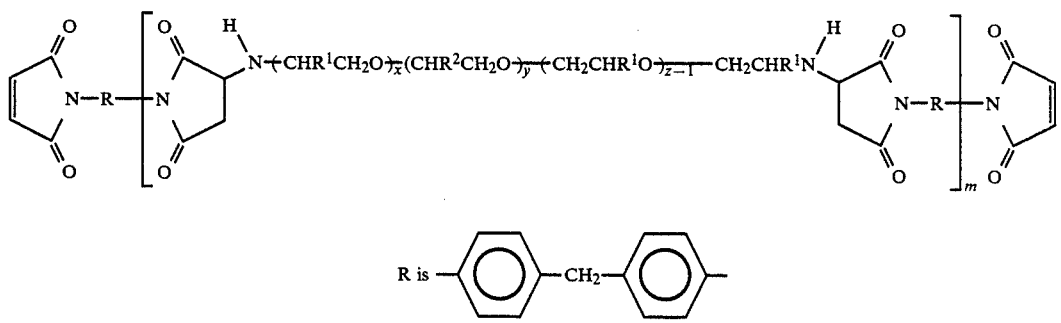

wherein $R^1$ and $R^2$ are independently alkyl or hydrogen, x, y, and z depend on the amine used, and m is predominantly 1.

DETAILED DESCRIPTION

Novel bismaleimide derivatives of higher molecular weight polyoxyalkyleneamines represented by the formula:

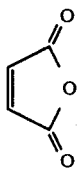

R is $CH_2CH_2-(OCH_2CH_2)_n$ wherein x, y, and z depend on the amine used, wherein when $R^1$=methyl or ethyl, x=1 to 70 and y=z=0; and when $R^1$=methyl or ethyl and $R^2$=H, then x+z=2.5 and y=5 to 80 n is 1, 2, or 3, m is 0 to several and predominantly 1, and $R^1$ and $R^2$ are independently alkyl or hydrogen.

$$H_2NCH_2CH_2-(-OCH_2CH_2-)_n-NH_2 \quad (I)$$

where n=1, 2 or 3 which is combined with maleic anhydride of the formula:

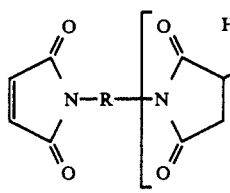
(II)

to form a bismaleamic acid of the formula:

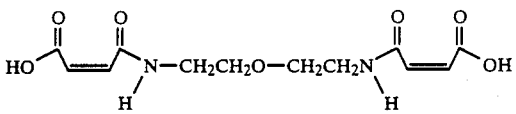

which is reacted with acetic anhydride in the presence of acetone solution to form a bismaleimide of the formula:

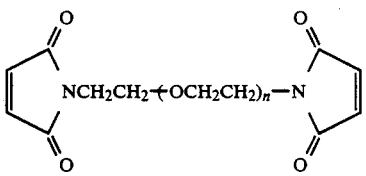

where n=1, 2 or 3 which is subsequently reacted with a polyoxyalkyleneamine with a molecular weight greater than 200.

In another embodiment aromatic bismaleimide derivatives are prepared by reaction of polyoxyalkyleneamines with commercially available aromatic bismaleimides. These materials are useful in the preparation of homopolymers and copolymers that may be suitable as matrix resins in composites. This can be represented by the following:

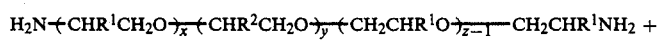

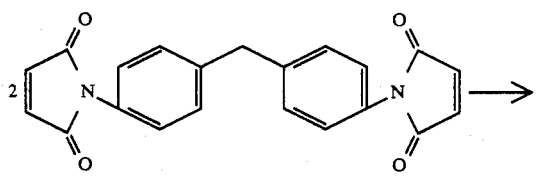

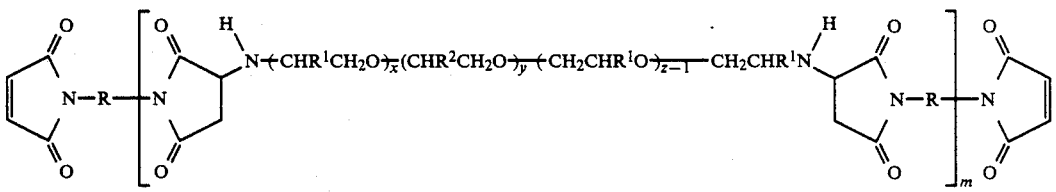

R is 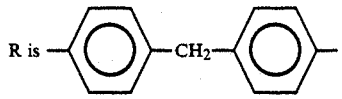

wherein $R^1$ and $R^2$ are independently alkyl or hydrogen, x, y, and z depend on the amine used, n is 1, 2, or 3, and m is predominantly 1.

Preparation of monomers containing polyoxyalkylene backbones and aromatic bismaleimide termination in this second embodiment is much easier than by the direct route (reaction of the polyoxyalkyleneamine with maleic anhydride); from these monomers bismaleimide copolymers and homopolymers may be prepared by several methods.

Diamine Starting Materials

The oxyethylene diamine reactants for the first embodiment represented by (I) above include di-, tri-, and tetraethylene glycol diamine compounds.

Of special note are the "JEFFAMINE ® EDR series diamines". The structure of "JEFFAMINE ® EDR" can be generically illustrated as follows:

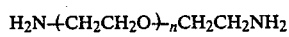

H$_2$N—(CH$_2$CH$_2$O)$_n$—CH$_2$CH$_2$NH$_2$ where n=2 or 3.

In one example the diamine used is JEFFAMINE ® EDR-148. JEFFAMINE ® EDR-148 is the trademark for a triethylene glycol diamine produced by Texaco Chemical Co..

Preparation of the bismaleimides is effected by reacting a diamine with 2 moles of maleic anhydride. These reactants are mixed with a small amount of solvent to facilitate the mixing process which solvent is subsequently driven off once the bismaleimide is formed.

Preparation of the Bismaleimides

The bismaleimide product is preferentially formed when a bis(amic acid) (prepared from the oxyethylene diamines and maleic anhydride) is reacted with an excess of anhydride at autogenous pressure at a temperature within the range of about 50° to about 150° C. for a reaction time within the range of about 0.5 to about 12 hours. Good results are obtained heating the mixture at 60° to 100° for 0.5 to 4 hours to provide complete reaction of the diamine and the anhydride. Normally, the reaction will go to completion after a reaction time within the range of about 1-2 hours.

The reaction is complete when essentially all of the diamine has reacted with the maleic anhydride. Under the noncatalytic reaction conditions employed herein, the amine groups of the polyoxyalkylene diamine are essentially unreactive with each other.

The bismaleimide monomers and prepolymers that are formed by the process are liquid or solid materials having a molecular weight within the range of about 250 to about 6000 and containing no terminal primary amine groups.

The reaction mixture will comprise a diamine addition product which may be generally characterized by the following formula:

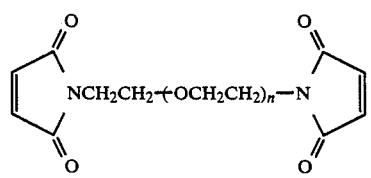

wherein n represents 1, 2 or 3.

A variety of molecular configurations is possible for the bismaleimides, depending on the starting materials. For example, where the starting materials are bisamino-ethyl ether and maleic anhydride, the bismaleimide will have the formula:

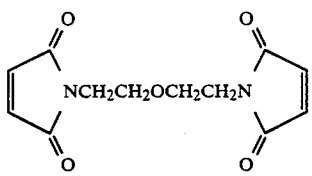

Where the diamine is JEFFAMINE ® EDR-148 and the anhydride is maleic anhydride, the reaction product will be composed principally of a bismaleimide having the formula:

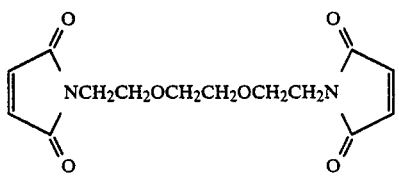

In accordance with the present invention the bismaleimides formed by the processes described above are subsequently reacted with high molecular weight polyoxyalkylene amines to provide the bismaleimide derivatives of higher molecular weight polyoxyalkyleneamines.

The Polyoxyalkyleneamines

Generally polyoxyalkyleneamines which will work are those with a molecular weight of greater than 200.

One group of suitable amines are polyoxyalkylenediamines of the formula:

NH$_2$CH(CH$_3$)CH$_2$—[OCH$_2$CH(CH$_3$)]$_x$—NH$_2$

Compounds having the above formula include JEFFAMINE ® D series diamines which are based on a polypropylene glycol (PPG) backbone and are available in a variety of molecular weights. They are low viscosity, light-colored liquids exhibiting low vapor pressure and high primary content. D-series amines include D-230, D-400 and D-2000 with approximate molecular weights of 230, 400 and 2000 respectively. Good results were obtained using D-400 as demonstrated in Example I.

Another group which can be used is water-soluble diamines based on a predominantly polyethylene glycol (PEG) backbone of the formula:

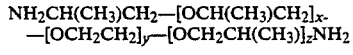

NH$_2$CH(CH$_3$)CH$_2$—[OCH(CH$_3$)CH$_2$]$_x$—
—[OCH$_2$CH$_2$]$_y$—[OCH$_2$CH(CH$_3$)]$_z$NH$_2$

Polyoxyethylenediamines having this formula include the JEFFAMINE ®-ED series diamines. ED series include ED-600, ED-900 and ED-2000, having approximate molecular weights of 600, 900 and 2000 respectively.

Aromatic Bismaleimides

Where aromatic bismaleimide derivatives of polyoxyalkyleneamines are the desired product suitable aromatic bismaleimides can be selected from among those which are commercially available.

One suitable aromatic bismaleimide has the formula:

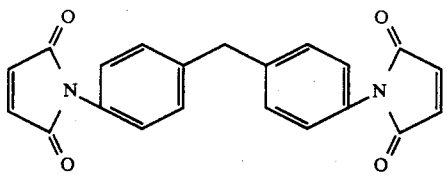

Other examples include bismaleimides of 2,4-toluenediamine, 4,4'-diaminodiphenylmethane, 1,4-diaminobenzene and 1,3-diaminobenzene.

One aromatic bismaleimide which works well is 4,4'-bismaleimidodiphenylmethane (MDABMI), shown above.

Preparation of the Bismaleimide Derivatives

According to the instant invention novel bismaleimides are prepared by reacting low molecular weight oxyethylenediamines with higher molecular weight polyoxyalkyleneamines to form bis(maleimidoaspartimide) compounds. As mentioned the reaction is a Michael addition. The reaction works particularly well with propylene oxide capped polyoxyalkyleneamines. The low molecular weight bismaleimides react with the propylene oxide capped diamines in a 2/1 ratio to give bis-Michael adducts.

In the method of the instant invention the bismaleimide is dissolved in chloroform and the polyoxyalkyleneamine is gradually added. The resulting solution is stirred at a temperature of from 20° to 140° C. with the preferred range being 40°-80° C. for a period of from 1 to 4 hours. The chloroform is then removed under vacuum with the temperature kept below 55° C. In most cases the product is a liquid at room temperature.

In the method of this invention, the pressure may range from 0.5 atm to 50 atm. The preferred pressure is atmospheric.

Preparation of the aromatic bismaleimide derivatives should be carried out under a temperature of from 45° C. to 75° C. The preferred temperature is under approximately 125° C.

The products resulting from this method are used to make polymers by reacting them at a temperature of at least 150° C. for about 30 minutes to 2 hours in the presence of either an additional amount of the higher molecular weight bismaleimide derivative or in the presence of a suitable copolymer.

The following examples are given in the way of illustration only and are not intended as limitations on the scope of the invention.

Examples I through IV demonstrate the preparation of bismaleimide derivatives of higher molecular weight polyoxyalkyleneamines.

In these preparations the diamine (neat or in chloroform solution) is added to a chloroform solution of the oxyethylene bismaleimide. The following illustrates the procedure for two different polyoxyalkyleneamines.

EXAMPLE I

The bismaleimide of bisaminoethyl ether (24.5 g, 93 mmol) was dissolved in 175 ml chloroform at 55° C. in a 500 ml 3-necked round bottomed flask; the D-400 (18.6 g, 46 mmol) was added over a 10 minute period. The resulting solution was heated at 55° C. for an hour and then allowed to sit at room temperature overnight. The chloroform was removed under vacuum, with the temperature kept below 55° C., leaving a tan paste, 47 g, 110% (chloroform not entirely removed). The nmr analysis of this material was as expected for the desired product.

EXAMPLE II

The bismaleimide of JEFFAMINE ® EDR-148 (triethylene glycol diamine) 14.1 g, 45.8 mmol) was dissolved in 100 ml chloroform in a 250 ml 3-necked round-bottomed flask. The ED-900 (20.0 g, 22.2 mmol) was added in a steady stream, and the resulting orange solution was heated at 65° C. for 2.5 hours. The chloroform was then removed under vacuum, with the temperature kept below 55° C., giving a viscous, rather turbid brown liquid, 33.1 g, 97%. The proton nmr spectrum of this material was as expected for the desired product.

Use of these products in preparation of polymers, both alone and with other bismaleimides, is illustrated in the following examples:

EXAMPLE III

The product of Example II above (1.0 g) was heated with the bismaleimide of JEFFAMINE ® EDR-148 (1.0 g) at 185° C. for 45 min. The product was a clear, hard, dark orange polymer with a decomposition temperature of 380° C. determined by tga in nitrogen.

EXAMPLE IV

The product from Example I above (2.6 g) was heated at 180° C. (after a brief initial heating to 215° C.) for one hour. The product was a clear, flexible, orange polymer with a decomposition temperature of 270° C. determined by tga in nitrogen.

Examples V through IX demonstrate the method of producing an aromatic bismaleimide derivative and the use of the products in homopolymerization and copolymerization. In a general preparation of the compounds of this invention, a chloroform solution of the polyoxyalkylene diamine is added to a chloroform solution of the aromatic bismaleimide. The resulting solution is optionally heated and then concentrated under vacuum to afford the bismaleimide product, which can be polymerized.

EXAMPLE V

Reaction of JEFFAMINE ® D-400 with 4,4'-bismaleimidodiphenylmethane (MDABMI):

The MDABMI (8.52 g, 23.8 mmol) was dissolved in 45 ml chloroform at 40° in a 250 ml 3-necked round-bottomed flask under nitrogen. A solution of JEFFAMINE ® D-400 (4.81 g, 12.0 mmol) in 5 ml chloroform was added dropwise over a 5-10 minute period, resulting in a darkening of the solution. The chloroform was removed under vacuum, with the solution heated in a hot water bath, leaving 12.5 g of glassy orange solid.

EXAMPLE VI

Reaction of JEFFAMINE ® ED-900 with MDABMI:

The MDABMI (6.00 g, 16.6 mmol) was dissolved in 40 ml chloroform at 45°. A solution of ED-900 (7.52 g, 8.35 mmol) in 5 ml chloroform was added dropwise over a 5-10 minute period; the resulting orange solution was stirred at 40°-45° for two hours, then concentrated under vacuum (heating with hot water bath) to 12.0 g of a very viscous orange liquid.

EXAMPLE VII

Reaction of JEFFAMINE® EDR-148 (triethyleneglycol diamine) with MDABMI:

The MDABMI (8.00 g, 22.3 mmol) was dissolved in 50 ml chloroform and heated to 40°. The EDR-148 (1.65 g, 11.1 mmol) was dissolved in 8 ml chloroform and added dropwise over a 10–15 minute period. The resulting solution was stirred at 40° for two hours, then filtered from a small amount of solid and concentrated under vacuum to a yellow glass that softened at approximately 90°–105°.

EXAMPLE VIII

Homopolymerization of JEFFAMINE® D-400/MDABMI adduct:

A 1.5 g sample of the glass was heated to 200° over a 45 min period and held at that temperature for 35 min. The product was a hard, opaque red polymer with a decomposition temperature not yet determined.

EXAMPLE IX

Copolymerization of JEFFAMINE® ED-600/MDABMI adduct with JEFFAMINE EDR-148/EDR-148 BMI adduct:

A mixture of 11.3 g of ED-600 adduct and 3.38 g of EDR-148/EDR-148 bismaleimide aduct was heated under vacuum at 65° C. for two hours and then poured into a 7"×3.25"×0.125" mold. The mold was heated in an oven at 160°–170° for 2.75 hr, and the product polymer was obtained as a red, semitransparent plaque with some voids resulting from evolution of volatiles. No properties have been determined.

EXAMPLES X–XXII

Small samples of some of the polymers were prepared from these materials by heating the prepolymers in a rectangular mold in air at 170°–185°. A brief description of their properties is given in the table below. Amine(s) refers to the amine reacted with the BMI source (Michael acceptor).

| Example | amine(s) | BMI source | properties |
|---|---|---|---|
| X | D-2000 | MDA | red, flexible, inelastic |
| XI | T-5000 | EDR-148 | orange, flexible, elastic |
| XII | D-400 | EDR-148 | red, flexible, inelastic |
| XIII | ED-900 | EDR-148 | brown, flexible, slightly elastic |
| XIV | T-403 | EDR-148 | red, somewhat flexible, inelastic |
| XV | D-400 | BAEE | red, flexible, inelastic |
| XVI | T-5000 | MDA/BAEE | clear, yellow, elastic |
| XVII | D-400/T-403 | EDR-148 | clear, red, flexible |
| XVIII | ED-2001 | EDR-148 | orange, translucent, rather flexible, inelastic |
| XIX | EDR-148/D-4000 | EDR-148 | brown, opaque, very flexible and elastic |
| XX | EDR-148/T-5000 | EDR-148 | brown, opaque, flexible and strong |
| XXI | ET-3000 | EDR-148 | transparent, flexible, elastic |
| XXII | D-230 | EDR-148 | red, translucent, somewhat flexible, inelastic |

Amines and BMI sources beginning with D-, T-, ED-, EDR-, or ET- refer to the JEFFAMINE amine products designated as shown. BAEE is bis(aminoethyl)ether and MDA is 4,4'-methylene dianiline. In Example XVI the molar ratio of MDA to BAEE is 1:1.

What is claimed is:

1. Novel bismaleimide derivatives of higher molecular weight polyoxyalkyleneamines of the formula:

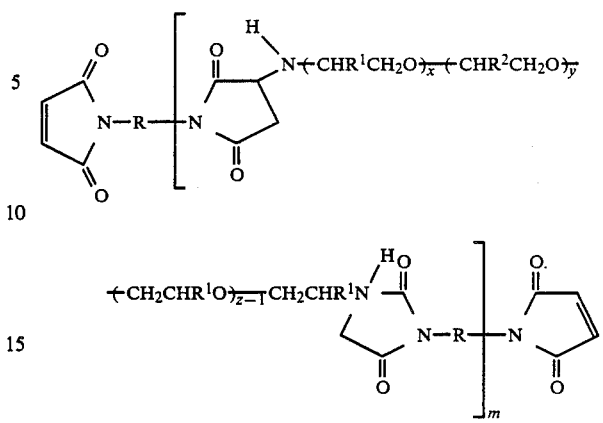

where R is $CH_2CH_2-(OCH_2CH_2-)_n$ and wherein $R^1$ and $R^2$ are independently lower alkyl or hydrogen and x, y and z depend on the amine used, wherein when $R^1=R^2=$methyl or ethyl then $x=1$ to 70 and $y=z=0$ and where $R^1=$methyl or ethyl and $R^2=H$, then $x+z \simeq 2.5$ and $y=5$ to 80; and n is 1, 2 or 3 and m is 0 to 1.

2. The compound in claim 1 wherein R represents an amine terminated triethylene glycol of the formula

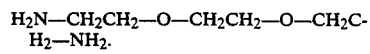

3. The compound in claim 1 wherein R represents an amine terminated tetraethylene glycol of the formula

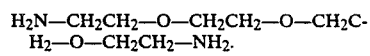

4. A bismaleimide having the formula:

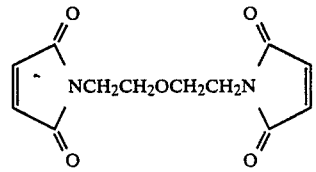

5. The compound of claim 1 wherein the group represented by R is selected from the group consisting of diethylene glycol diamine, triethylene glycol diamine and tetraethylene glycol diamine.

6. The compound of claim 1 wherein R is selected from the group consisting of a bisaminoethylether, an amine terminated triethylene glycol of the formula

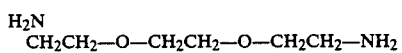

and an amine terminated tetraethylene glycol of the formula

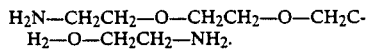

7. A novel aromatic bismaleimide derivative of the formula:

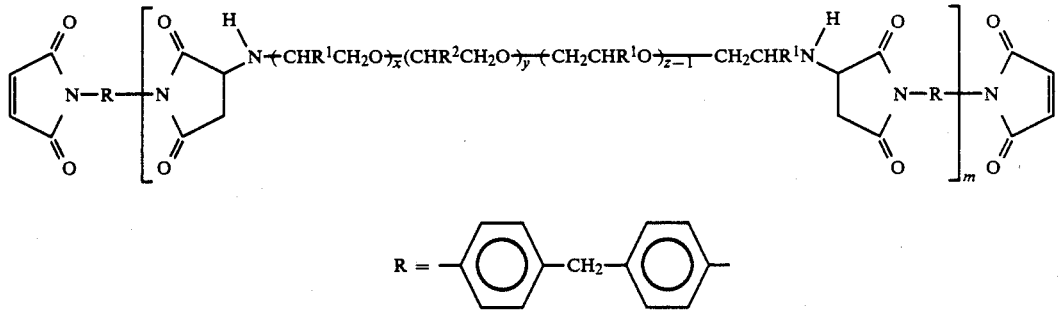

wherein $R^1$ and $R^2$ are independently alkyl or hydrogen, x, y, and z depend on the amine used, and m is 0 to 1.